United States Patent
Boudin et al.

(10) Patent No.: US 10,142,565 B2
(45) Date of Patent: *Nov. 27, 2018

(54) FLASH THERMOGRAPHY BORESCOPE

(71) Applicant: Siemens Energy, Inc., Orlando, FL (US)

(72) Inventors: Dustin C. Boudin, Belmont, NC (US); Clifford Hatcher, Jr., Orlando, FL (US); Anand A. Kulkarni, Charlotte, NC (US)

(73) Assignee: SIEMENS ENERGY, INC., Orlando, FL (US)

( * ) Notice: Subject to any disclaimer, the term of this patent is extended or adjusted under 35 U.S.C. 154(b) by 152 days.

This patent is subject to a terminal disclaimer.

(21) Appl. No.: 15/354,004

(22) Filed: Nov. 17, 2016

(65) Prior Publication Data

US 2017/0070686 A1    Mar. 9, 2017

Related U.S. Application Data

(63) Continuation-in-part of application No. 14/684,471, filed on Apr. 13, 2015.

(51) Int. Cl.
*H04N 5/33* (2006.01)
*H04N 7/18* (2006.01)
(Continued)

(52) U.S. Cl.
CPC ........... *H04N 5/33* (2013.01); *A61B 1/00064* (2013.01); *G02B 23/24* (2013.01);
(Continued)

(58) Field of Classification Search
None
See application file for complete search history.

(56) References Cited

U.S. PATENT DOCUMENTS 6,992,315 B2   1/2006   Twerdochlib
7,554,086 B2 * 6/2009   Shepard ................. G03B 41/00
                                                      250/341.1
(Continued)

FOREIGN PATENT DOCUMENTS

EP   2413094 A1   2/2012
GB   2354836 A    4/2001

OTHER PUBLICATIONS

U.S. Appl. No. 14/684,471, filed Apr. 13, 2015, and entitled System to Prognose Gas Turbine Remaining Useful Life.
(Continued)

*Primary Examiner* — Mohammad J Rahman

(57) ABSTRACT

A flash thermography device for generating an infrared image of each of a plurality of rotating turbine components located inside a turbine. The device includes an infrared sensor for detecting thermal energy radiated by each component. The device also includes a borescope having a viewing end located on a longitudinal axis of the borescope. The borescope is positioned in an inspection port to locate the viewing end inside the turbine such that at least one component is within a field of view of the viewing end. In addition, the device includes a flash source that generates a plurality of light pulses corresponding to the number of components that rotate during a single rotation of the rotor, wherein the light pulses are oriented substantially transverse to the longitudinal. Thermal energy radiated from each component is transmitted through the borescope to the infrared sensor to enable generation infrared images.

24 Claims, 9 Drawing Sheets

(51) Int. Cl.
*G02B 23/24* (2006.01)
*H04N 5/225* (2006.01)
*A61B 1/00* (2006.01)

(52) U.S. Cl.
CPC ....... *G02B 23/2492* (2013.01); *H04N 5/2256* (2013.01); *G02B 23/2453* (2013.01); *H04N 2005/2255* (2013.01)

(56) References Cited

U.S. PATENT DOCUMENTS

| | | | |
|---|---|---|---|
| 7,654,145 B2 | 2/2010 | Twerdochlib | |
| 7,769,201 B2 | 8/2010 | Sun | |
| 7,861,592 B2 | 1/2011 | Twerdochlib | |
| 9,057,710 B2 | 6/2015 | Hatcher et al. | |
| 9,154,743 B2 | 10/2015 | Hatcher, Jr. et al. | |
| 2005/0056786 A1* | 3/2005 | Shepard | G01N 25/72 250/341.4 |
| 2005/0085698 A1* | 4/2005 | Bonningue | A61B 1/00183 600/170 |
| 2005/0270519 A1 | 12/2005 | Twerdochlib | |
| 2012/0050537 A1* | 3/2012 | Ringermacher | G01B 11/0658 348/164 |
| 2013/0194413 A1 | 8/2013 | Hatcher | |
| 2014/0267694 A1 | 9/2014 | Henderkott et al. | |
| 2015/0300920 A1 | 10/2015 | DeAscanis et al. | |
| 2016/0018292 A1 | 1/2016 | DeAscanis et al. | |
| 2016/0301880 A1 | 10/2016 | Iyer et al. | |

OTHER PUBLICATIONS

U.S. Appl. No. 15/180,364, filed Jun. 13, 2016, and entitled Flash Thermography Device for Inspecting Turbine Components.
U.S. Appl. No. 15/252,520, filed Aug. 31, 2016, and entitled Flash Thermography Device Having Moveable Arm for Inspecting Internal Turbine Components.
U.S. Appl. No. 15/252,565, filed Aug. 31, 2016, and entitled Blackbody Material Application System for a Turbine.
PCT International Search Report and Written Opinion of International Searching Authority dated Jan. 19, 2018 corresponding to PCT International Application No. PCT/US2017/055462 filed Oct. 6, 2017.

* cited by examiner

FLASH THERMOGRAPHY BORESCOPE

CROSS REFERENCE TO RELATED APPLICATIONS

This application is a continuation-in-part under 35 U.S.C. § 120 of copending U.S. patent application entitled "SYSTEM TO PROGNOSE GAS TURBINE REMAINING USEFUL LIFE", filed on Apr. 13, 2015, U.S. application Ser. No. 14/684,471, which is incorporated herein by reference in its entirety and to which this application claims the benefit of priority.

FIELD OF THE INVENTION

This invention relates to flash thermography devices used in connection with turbines, and more particularly, to a flash thermography device having an infrared sensor and a borescope wherein the borescope is positioned in an inspection port so as to locate a viewing end of the borescope inside the turbine such that at least one rotating component of the turbine is within a field of view of the viewing end and wherein the borescope includes a flash source that generates a plurality of light pulses corresponding to the number of components that rotate during a single rotation of the rotor to enable generation of an infrared image of each component.

BACKGROUND OF THE INVENTION

In various multistage turbomachines used for energy conversion, such as gas turbines, a fluid is used to produce rotational motion. Referring to FIG. 1, an axial flow gas turbine 10 includes a compressor section 12, a combustion section 14 and a turbine section 16 arranged along a horizontal center axis 18. The compressor section 12 provides a compressed air flow to the combustion section 14 where the air is mixed with a fuel, such as natural gas, and ignited to create a hot working gas. The turbine section 16 includes a plurality of turbine blades 20 arranged in a plurality of rows. The hot gas expands through the turbine section 16 where it is directed across the rows of blades 20 by associated stationary vanes 22. The blades 20 are each configured as a blade assembly that is attached to a shaft that is rotatable about the center axis 18. As the hot gas passes through the turbine section 16, the gas causes the blades 20 and thus the shaft to rotate, thereby providing mechanical work. Each row of blades 20 and associated vanes 22 form a stage. In particular, the turbine section 16 may include four rows of blades 20 and associated vanes 22 to form four stages. The gas turbine 10 further includes an exhaust cylinder section 24 located adjacent the turbine section 16 and an outer diffuser section 26 located adjacent the exhaust cylinder section 24.

Sections of the turbine 10 that are exposed to the hot gases as the gases travel along a hot gas path in the turbine 10 may include a ceramic-based coating that serves to minimize exposure of the base metal of a component, such as an airfoil base metal, to high temperatures that may lead to oxidation of the base metal. Such a coating may be a known thermal barrier coating (TBC) that is applied onto a bond coating (BC) formed on the base metal.

A turbine 10 is typically operated for extended periods. The TBC layer or both the TBC and BC layers may undesirably deteriorate or delaminate during operation of the turbine 10. This exposes the base metal to high temperatures, which may lead to oxidation of the base metal. A turbine is inspected at periodic intervals to check for wear, damage and other undesirable conditions that may have occurred with respect to various internal components. In addition, the TBC/BC layers are inspected to determine the degree of deterioration of the TBC/BC layers (i.e. remaining thickness of the layers) and other undesirable conditions. In order to inspect components within the turbine 10, the turbine 10 is shut down and allowed to cool down, which takes a substantial amount of time. An inspection/evaluation team must then disassemble substantial portions of the turbine 10, such as an outer casing 34 and associated components, in order to gain access to a desired internal turbine component which is then removed and shipped to a laboratory in order to perform an assessment or inspection of the turbine component. However, the current procedure for inspection is labor intensive, time consuming and expensive. Further, the current procedure limits the number of opportunities available for performing a nondestructive assessment or inspection of the turbine 10.

SUMMARY OF INVENTION

A flash thermography device is disclosed for generating an infrared image of each of a plurality of turbine components attached to a rotor, wherein rotation of the rotor causes rotation of the components and the turbine includes at least one inspection port. The device includes an infrared sensor for detecting thermal energy radiated by each component. The device also includes a borescope having at least one lens positioned between sensor and viewing ends, wherein the at least one lens and the sensor and viewing ends are located on a longitudinal axis of the borescope. The sensor end is located adjacent the infrared sensor and the borescope is positioned in the inspection port to locate the viewing end inside the turbine such that at least one component is within a field of view of the viewing end. Further, the device includes a flash source that generates a plurality of light pulses corresponding to the number of components that rotate during a single rotation of the rotor, wherein the light pulses are oriented substantially transverse to the longitudinal axis. Each light pulse heats a corresponding component wherein thermal energy radiated from each component is transmitted through the borescope to the infrared sensor to enable generation of an infrared image of each component.

BRIEF DESCRIPTION OF DRAWINGS

The teachings of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
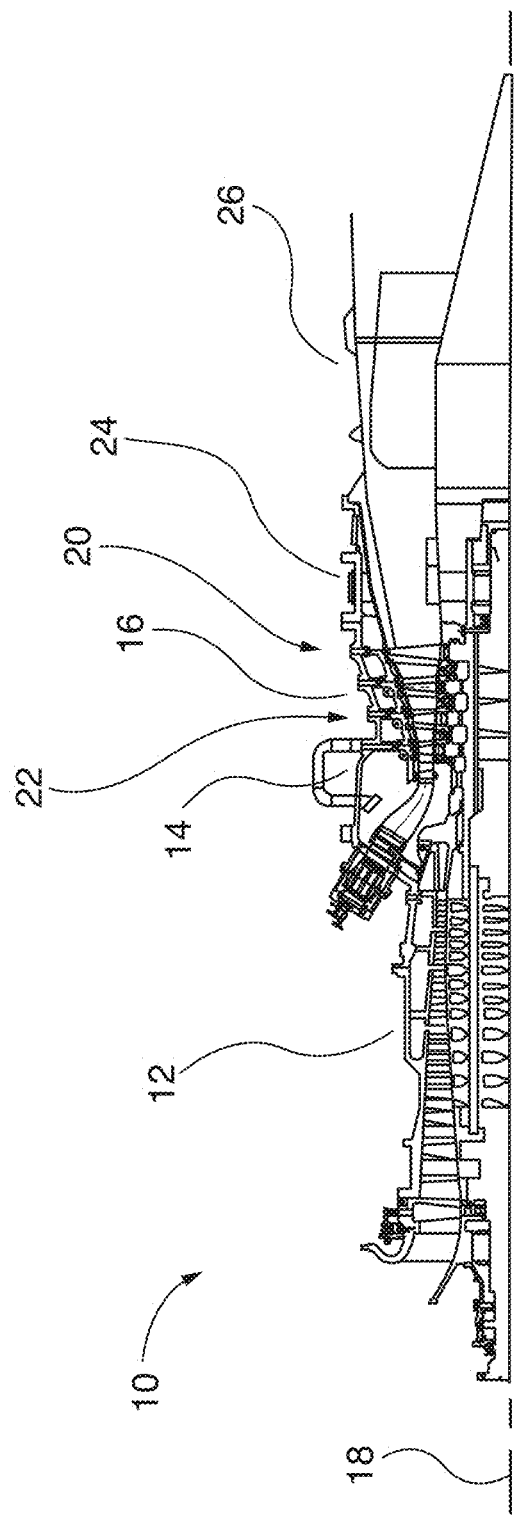
FIG. 1 is a partial view an axial flow gas turbine.

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

The disclosures of U.S. Pat. No. 9,057,710, issued Jun. 16, 2015, entitled SYSTEM AND METHOD FOR AUTOMATED OPTICAL INSPECTION OF INDUSTRIAL GAS TURBINES AND OTHER POWER GENERATION MACHINERY to Clifford Hatcher et al. and assigned to SIEMENS ENERGY, INC., U.S. Pat. No. 9,154,743, issued Oct. 6, 2015, entitled SYSTEM AND METHOD FOR OPTICAL INSPECTION OF OFF-LINE INDUSTRIAL GAS TURBINES AND OTHER POWER GENERATION MACHINERY WHILE IN TURNING GEAR MODE to Clifford Hatcher et al. and assigned to SIEMENS ENERGY, INC., U.S. Patent Publication No. 20150300920, published Oct. 22, 2015, entitled METHOD AND SYSTEM FOR SURFACE PROFILE INSPECTION OF OFF-LINE INDUSTRIAL GAS TURBINES AND OTHER POWER GENERATION MACHINERY to Joshua DeAscanis et al. and assigned to SIEMENS ENERGY, INC., and U.S. Patent Publication No. 20160018292, published Jan. 21, 2016, entitled GAS TURBINE INSPECTION APPARATUS AND METHOD AND SYSTEM FOR INSPECTING A GAS TURBINE to Joshua DeAscanis et al. and assigned to SIEMENS ENERGY, INC. are each incorporated by reference in their entirety.

Figure 2:
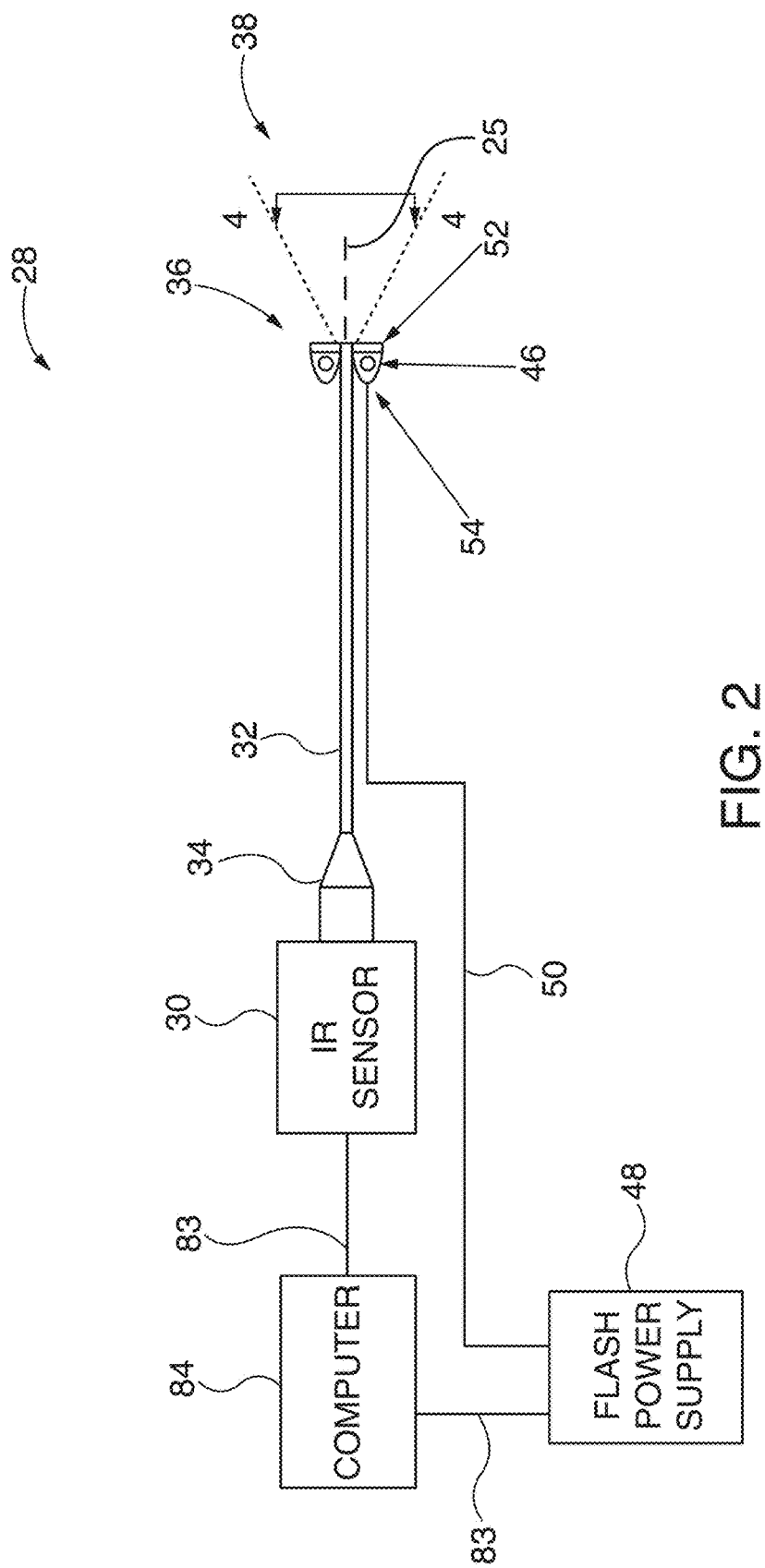
FIG. 2 depicts a flash thermography device in accordance with an embodiment of the invention.

Referring to FIG. 2 a flash thermography device 28 in accordance with an embodiment of the invention is shown, The device 28 includes an infrared (IR) sensor 30 for detecting thermal energy in the infrared region of the electromagnetic spectrum. In an embodiment, the IR sensor 30 is an IR camera such as a digital single lens reflex (D-SLR) camera although it is understood that other types of IR sensors may be used. By way of example, the IR sensor 30 may be an IR camera such as that available from FUR Systems, Boston, Mass., US. The device 28 is configured to capture IR images of internal portions of a turbine 10.

Figure 3:
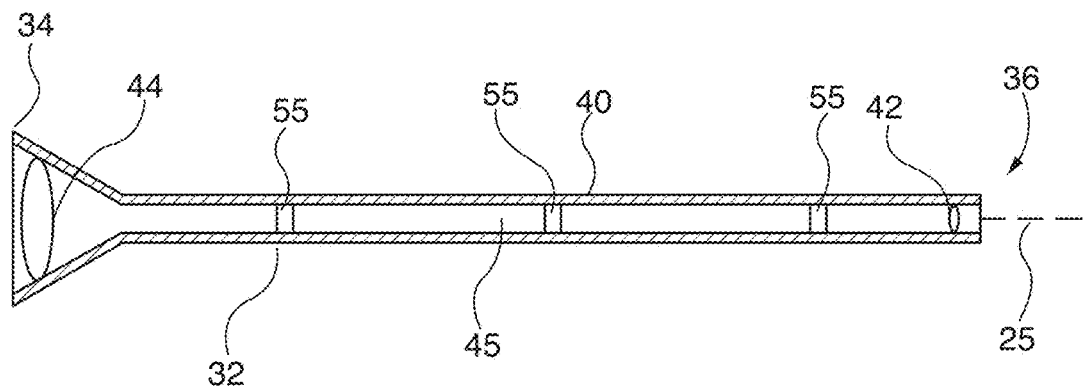
FIG. 3 is a cross sectional side view of a borescope of the device.

The device 28 also includes a borescope 32 having a sensor end 34 that is attached to the IR sensor 30 and a viewing end 36 that provides a field of view 38 for the IR sensor 30. Referring to FIG. 3, a cross sectional side view of the borescope 32 is shown. The borescope 32 includes a rigid tube 40 having a longitudinal axis 25 and an interior hollow portion 45 that extends through the tube 40 between the sensor end 34 and the viewing end 36. A first lens 42 is located in the viewing end 36 and a second lens 44 at the sensor end 34 that is adjacent the IR sensor 30. In an embodiment, the first 42 and second lenses 44 are each objective lenses although it is understood that other types of lenses may be used. Further, the first lens 42 may be a different type of lens than the second lens 44. In addition, the borescope 32 may include additional lenses such as least one relay lens 55 or other suitable lens or optical device (i.e. prism, mirror) or combination thereof to ensure that thermal energy radiated by a workpiece is transmitted from the viewing end 36 to the IR sensor 30. In an embodiment, the lenses 42, 44, 55 may be fabricated from germanium although it is understood that other materials or combination of materials may be used. In an alternate embodiment, the tube 40 is flexible.

Referring back to FIG. 2, a flash source 46 that provides a high intensity light pulse is located on the viewing end 36 of the borescope 32. In an embodiment, the flash source 46 is a flash tube although it is understood that other types of flash sources may be used. The flash source 46 is energized by a flash power supply 48 via an electrical connection 50 that may include wires or cables. In an embodiment, the flash power supply 48 has power rating of approximately 1000 to 5000 Joules. When energized, the flash source 46 emits a high intensity light pulse across a work piece that serves to heat the work piece. A portion of the thermal energy radiated by the work piece is then transmitted through the first lens 42, the hollow portion 45 and second lens 44 and is detected by the IR sensor 30. The borescope 32 includes an IR filter 52 located on the viewing end 36 to enable detection by the IR sensor 30 of thermal energy that is in the middle infrared region of the electromagnetic spectrum. The IR sensor 30 is configured to generate IR images of the work piece based on the radiated thermal energy. The IR sensor 30 may also be configured to obtain image data at other frequencies in addition to or in place of the infrared region of the electromagnetic spectrum. Further, the borescope 32 may include a reflector 54 located on the viewing end 36 for directing and concentrating the light pulse in a desired direction toward the work piece.

Figure 4:
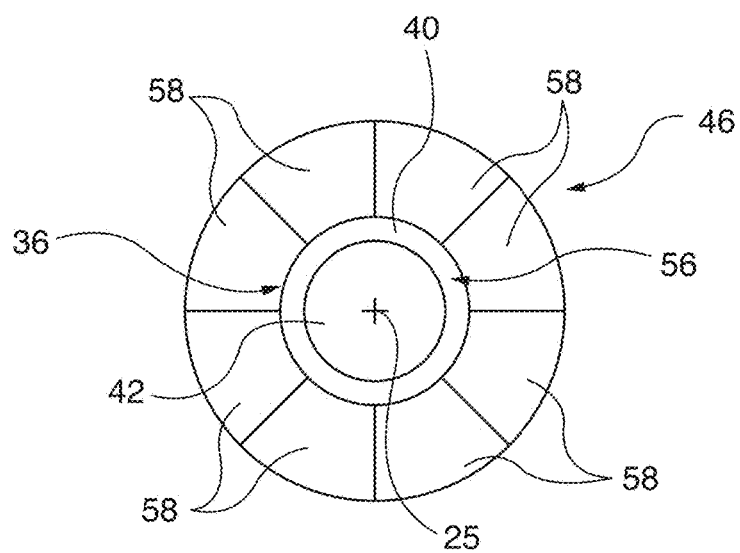
FIG. 4 depicts a viewing end of the borescope along view line 4-4 of FIG. 3.

Referring to FIG. 4, a view of the viewing end 36 of the borescope 32 along view line 4-4 of FIG. 3 is shown. The flash source 46 may have an annular shape including a central aperture 56 that receives the viewing end 36. In an alternate configuration, the flash source 46 may be comprised of a plurality of annular sectors 58. It is understood that other types of flash sources may be used such as white light emitting diodes.

Figure 5:
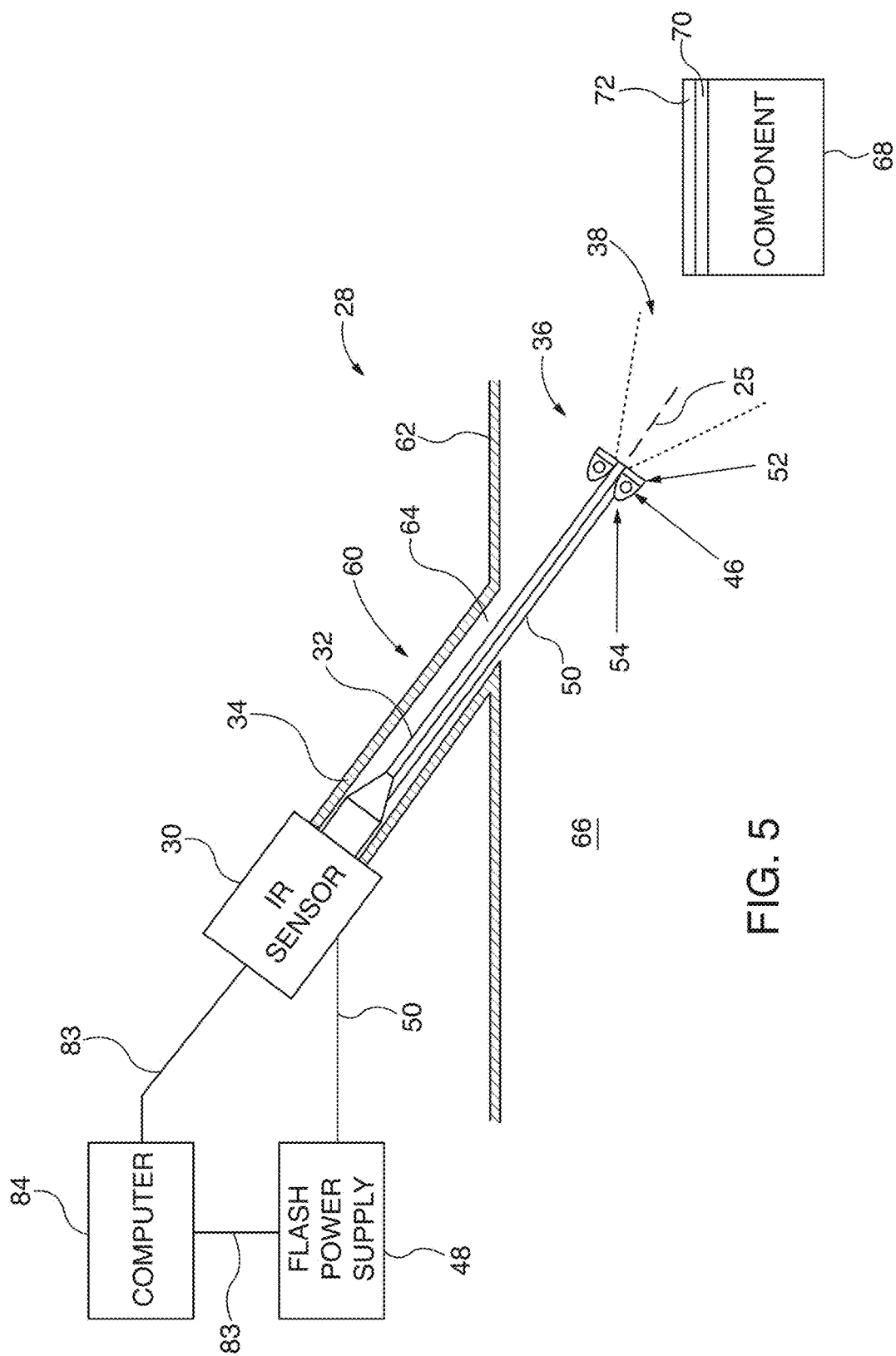
FIG. 5 is a partial cross sectional view of an exemplary inspection port.

A turbine includes a plurality of inspection ports located about a turbine periphery or outer casing. The inspection ports are positioned to enable inspection of various internal components and areas of the turbine without removal of an outer casing or covering of the turbine. By way of example, the inspection ports are located to enable inspection of combustors, transitions, transition exit mouth, row 1 vanes and blades and row 2 blades of a turbine. Referring to FIG. 5, a partial cross sectional view of an exemplary inspection port 60 is shown. The port 60 may be a preexisting port or a new port formed in an outer casing 62 of a turbine 10. The port 60 includes a through hole 64 that provides access to an interior 66 of the turbine 10. In an alternate embodiment, a plurality of inspection ports 60 may be used. For example, the inspection ports 60 may be located in a circumferential and/or staggered arrangement around the outer casing 62. In accordance with embodiments of the invention, the borescope 32 is inserted into the inspection port 60 such that the component 68 is within the field of view 38. In order to obtain an IR image of a component 68 such as an airfoil 20, the flash source 46 is energized by the flash power supply 48 thereby causing the flash source 46 to emit a light pulse that heats the component 68. A portion of the thermal energy radiated by the component 68 is then detected by the IR sensor 30. The IR sensor 30 generates IR images of the component 68 based on the thermal energy radiated by the component 68. Thus, IR images may be captured without removal of an outer casing 62 or other disassembly of the turbine 10 to gain access to the component 58. Further, the IR images may be obtained in situ, i.e. without having to remove the component 68 to be imaged from the turbine 10, which results in substantial time savings. In an embodiment the component 68 may be a hot gas path component such as a combustor, transition, vane 22, blade 20 or associated component.

It has been found by the inventors herein that IR images of a component 68 obtained by the device 28 provide sufficient detail of the internal features of the component 68 to enable evaluation by an inspection/evaluation team without the need for sectioning the component 68. Further, the device 28 generates IR images having sufficient detail to enable determination of a thickness of a BC 70 or TBC 72 layer formed on the component 68. Therefore, the current invention enables nondestructive evaluation (NDE) of turbine components, A turbine 10 is typically inspected at periodic intervals at which time the turbine is shut down. The device 28 enables the capturing of IR images of components 68 before the components 68 have cooled down, which results in further time savings. In particular, the flash source 46 sufficiently heats a desired component 68 so as to enable detection of radiated thermal energy by the IR sensor 30 while the component 68 is still relatively hot. In an embodiment, IR images may be taken within approximately five minutes of turbine shut down. Further, capturing an IR image takes relatively little time, for example, approximately five seconds.

Figure 6:
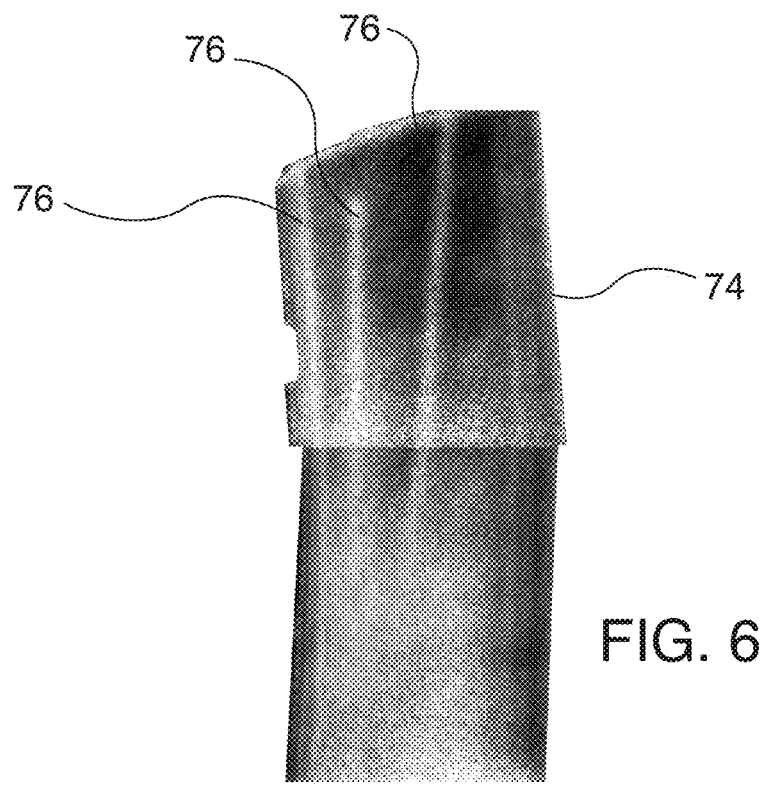
FIG. 6 depicts an infrared image of a stage 2 turbine blade that depicts internal cooling channels of the blade.
Figure 7:
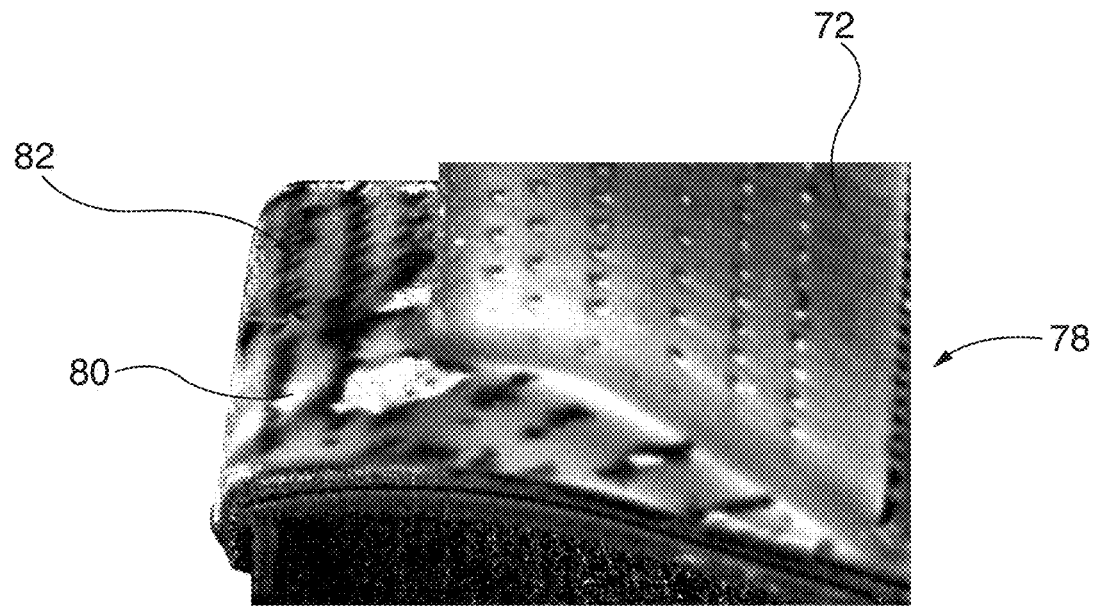
FIG. 7 depicts an infrared image of a thermal barrier coating layer for a stage 1 vane.

By way of example, FIG. 6 depicts an IR image of a stage 2 blade 74 that reveals internal cooling channels 76 of the blade 74. In addition, an IR image may be captured of a TBC layer 72 on stage 1 and stage 2 blades and/or stage 1 and stage 2 vanes that enables determination of the degree of spallation and/or delamination of the TBC layer 72. Referring to FIG. 7, an IR image of a TBC layer 72 for a stage 1 vane 78 is shown. Region 80 shows delamination of the TBC layer 72 that has occurred near cooling holes 82. FIG. 7 serves as a tomographic image that depicts the depth of the TBC layer 72. The device 28 enables a determination of the thickness of the BC 70/TBC 72 layers by an inspection/evaluation team to assess the extent of any chipping of the BC 70/TBC 72 layers that may have occurred. In particular, the disclosure of U.S. Pat. No. 7,769,201 is hereby incorporated by reference in its entirety.

If the BC 70/TBC 72 layers are acceptable, the turbine 10 is returned to service/operation without waiting for a time consuming cool down period and disassembly of the turbine 10. If there is significant damage to the BC 70/TBC 72 layers, the inspection/evaluation team can quickly make a decision to call for maintenance in order to avoid damage of a turbine component due to loss of BC 70/TBC 72 layers.

For example, a duration of the light pulse emitted by the flash source 46 is between approximately 2 to 15 milliseconds depending on the thickness of a BC 70 or TBC 72 layer. The length of time used for detecting the radiated thermal energy (i.e. signal collection time) is dependent upon the characteristics of the component 68 that is being imaged. With respect to BC 70/TBC 72 layers for example, the signal collection time for a thick coating (i.e. a thickness of approximately 600 µm to 2 mm) is longer than that for a thin coating (i.e. a thickness of approximately 150 µm to 600 µm). In an embodiment, the signal collection time for a thin coating when using an approximately 2 millisecond duration light pulse is approximately 2 seconds. The signal collection time for a thick coating when using an approximately 15 millisecond duration light pulse is approximately 15 seconds.

In another aspect, the current invention may also be used to obtain an IR image of the base metal, or metallic substrate, underneath the BC 70/TBC 72 layers. In order to obtain an IR image of the metallic substrate, an additional amount of heat needs to be generated in the metallic substrate. In an embodiment, a light pulse having a substantially longer duration is used to generate a sufficient amount of heat in the metallic substrate to obtain an IR image. For example, the duration of the light pulse may be approximately 1 to 2 minutes so as to form a relatively continuous flash. In particular, it has been determined that an increase in temperature in the metallic substrate of approximately 20 degrees C. generates a sufficient amount of heat for an IR image.

It has been found by the inventors herein that IR images of a metallic substrate provide a substantial amount of data about the metallic substrate that can be used to evaluate the condition of the metallic substrate. Similarly, IR images of metallic components that do not include BC 70/TBC 72 layers, such as later stage metallic components, may also be used to evaluate the condition of the metallic components.

The device 28 may also be used to capture IR images of cooling holes of an airfoil 20 or vane 22. During operation, the cooling holes of an airfoil 20 may become clogged due to compressor inlet debris that is drawn downstream into the turbine 10. By viewing an IR image of the cooling holes, the inspection/evaluation team can quickly assess the extent of any clogging of the cooling holes (i.e. whether the cooling holes are partially or fully clogged) and any impact that clogging would have upon continued operation of the turbine. In addition, the IR images may be used to generate three dimensional views of a cooling hole.

IR images may also be captured of stationary turbine components. For example, an IR image may be obtained of coated stationary turbine components including hot gas path components such as stage 1 or stage 2 vanes, transition piece and others. This enables evaluation or estimation of turbine characteristics such as back flow margin and the modulation of cooling flows. In particular, the turbine 10 may have been conservatively designed such that an initial level of cooling flow exceeds the level that is needed for sufficient cooling. The current invention may then be used to estimate back flow margin soon after shutdown without waiting for a cool down period to enable adjustment of cooling flow and improve turbine performance for future turbine operation. Further, an IR image may be obtained of coated rotating components such as hot stage 1 or stage 2 blades soon after a turbine shut down and without waiting for a cool down period. Impingement pressure ratios, which are indicative of base metal temperature changes of critical turbine components, such as hot gas path components, may also be estimated soon after a turbine shutdown and without waiting for a cool down period. This provides an opportunity for extending at least one service interval for the turbine 10 if the degree of deterioration of a turbine component is less than anticipated. Moreover, operation of the turbine 10 may be extended beyond nominal or expected limits due to the current invention, thus enabling extended service intervals with customers. In addition, the current invention enables forecasting or estimation of a remaining useful life of turbine components and TBC/BC layers without waiting for a cool down period and without disassembly of a portion of the turbine 10 such as turbine shell cover. Further, a firing temperature for the turbine 10 may be increased during operation of the turbine 10 based on an inspection of IR images of the turbine components, thus improving efficiency and power output. The current invention also enables monitoring of TBC/BC thickness/delamination levels which in turn enables prediction of whether the turbine 10 is able to withstand a level of chipping in the TBC/BC layers that may occur by estimation of base metal temperature. Information such as back flow measurement, pressure ratio and others may also be sent to a design team in real time to enable evaluation of current turbine cooling design and investigate possible design changes for improving efficiency and performance of the turbine. Further, IR images of turbine components may be captured during operation of the turbine.

Figure 8:
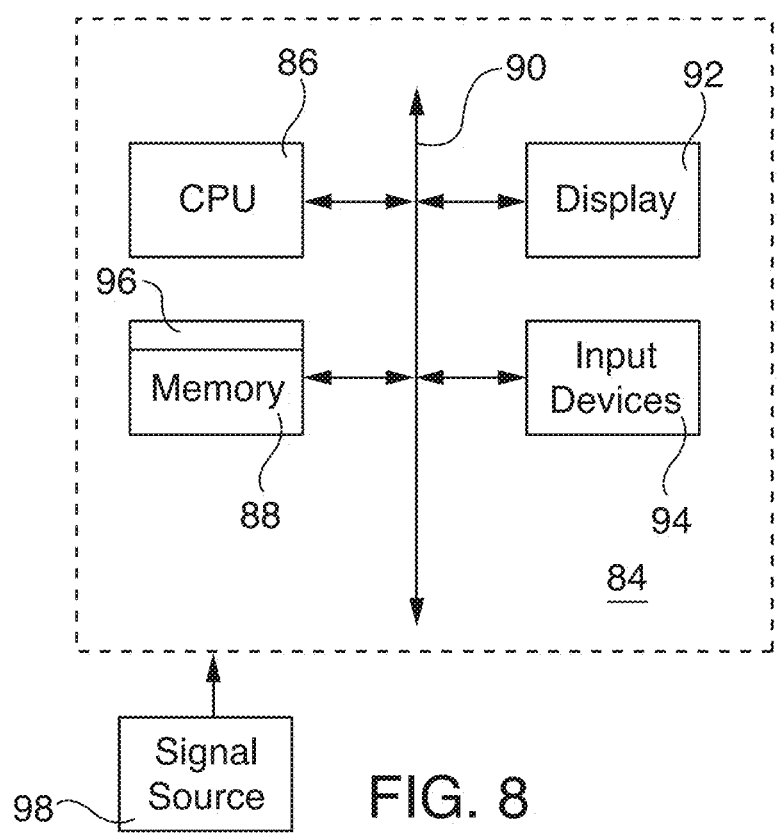
FIG. 8 is a block diagram of a computer.

Referring back to FIG. 2. the IR sensor 30 and flash power supply 48 are communicatively coupled to a computer 84 by a wired connection 83 or a wireless connection. The computer 84 includes software and drivers for controlling operation of the IR sensor 30, flash power supply 48 and flash source 46. The computer 84 may use well-known computer processors, memory units, storage devices, computer software, and other components. A high level block diagram of such a computer is illustrated in FIG. 8. Computer 84 may include a central processing unit (CPU) 86, a memory 88 and an input/output (I/O) interface 90. The computer 84 is generally coupled through the I/O interface 90 to a display 92 for visualization and various input devices 94 that enable user interaction with the computer 84 such as a keyboard, keypad, touchpad, touchscreen, mouse, speakers, buttons or any combination thereof. Support circuits may include circuits such as cache, power supplies, clock circuits, and a communications bus. The memory 88 may include random access memory (RAM), read only memory (ROM), disk drive, tape drive, etc., or a combination thereof. Embodiments of the present disclosure may be implemented as a routine 96 that is stored in memory 88 and executed by the CPU 86 to process the signal from a signal source 98. As such, the computer 84 is a general purpose computer system that becomes a specific purpose computer system when executing the routine 96. The computer 84 can communicate with one or more networks such as a local area network (LAN), a general wide area network (WAN), and/or a public network (e.g., the Internet) via a network adapter. One skilled in the art will recognize that an implementation of an actual computer could contain other components as well, and that FIG. 8 is a high level representation of some of the components of such a computer for illustrative purposes.

The computer 84 also includes an operating system and micro-instruction code. The various processes and functions described herein may either be part of the micro-instruction code or part of the application program (or a combination thereof) which is executed via the operating system. In addition, various other peripheral devices may be connected to the computer platform such as an additional data storage device and a printing device. Examples of well-known computing systems, environments, and/or configurations that may be suitable for use with computer 84 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

In some examples, the computer 84 is disposed within and considered a part of IR sensor 30 or display 92. In still other examples, the computer 84 may be co-located in both IR sensor 30 and display 92. In some examples, full 2D images of component 68, that is, composite 2D images that include all 360 degrees or some other desired portion of the external surfaces of component 68, are compiled from a plurality of individual images or exposures obtained by IR sensor 30 the subsequent inspection by a qualified NDE inspector/operator. In addition, in some examples, the computer 84 is configured to combine a plurality of images of component 68 captured by IR sensor 30, and form a composite image reflecting the image data of each of the plurality of images.

The device 28 may be inserted into an opening formed by removal of a component of the turbine 10 such as a pilot nozzle arrangement. As previously described, a turbine 10 also includes a plurality of inspection ports 60 located about a turbine periphery or outer casing 62. The inspection ports 60 are positioned to enable inspection of various internal components and areas of the turbine 10 without removal of the outer casing 62 or covering of the turbine 10. By way of example, the inspection ports 60 are located to enable inspection of combustors, transitions, transition exit mouth, row 1 vanes and blades and row 2 blades of a turbine. The inspection ports 60 may be located in a circumferential and/or staggered arrangement around the outer casing 62.

Figure 9:
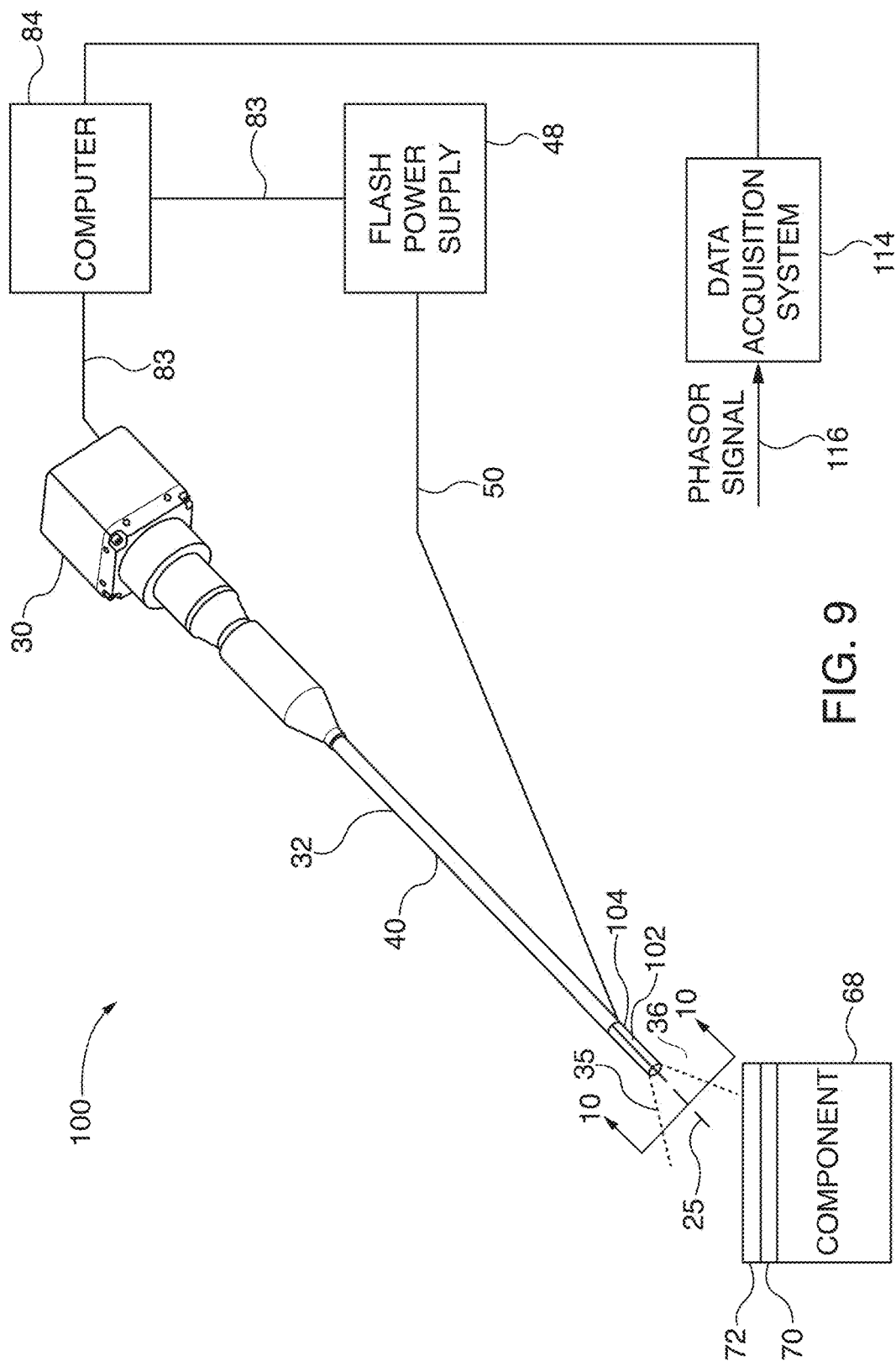
FIG. 9 depicts an alternate embodiment of the flash thermography device.
Figure 10:
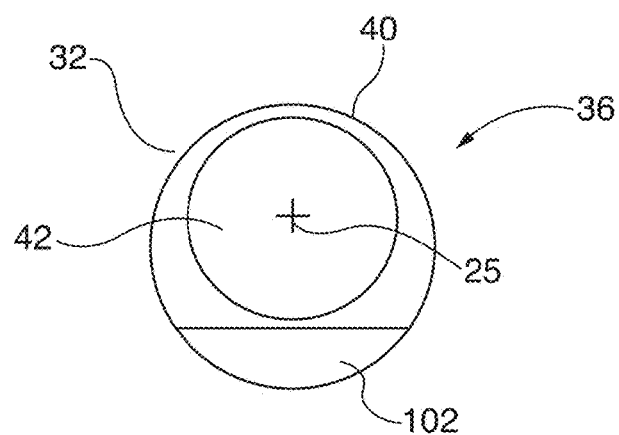
FIG. 10 is an end view of the tube along view line 10-10 of FIG. 9.

Many inspection ports 60 are substantially smaller in size than the opening formed by removal of a component such as a pilot nozzle arrangement. For example, an inspection port 60 may be 10 mm in diameter or smaller. Referring to FIG. 9, an alternate embodiment of a flash thermography device 100 suitable for insertion into a small inspection port 60 is shown. In this embodiment, the tube 40 is sufficiently small in size to enable insertion into a small inspection port 60. Further, the reduced tube size results in a narrow field of view 35 that is suitable for generating an IR image of cracks or other defects in a blade 20. FIG. 10 is an end view of the tube 40 along view line 10-10 of FIG. 9. Referring to FIG. 9 in conjunction with FIG. 10, the device 100 also includes a flash source 102 having a substantially elongated shape that is oriented to fit inside a cutout portion 104 of the tube 40 adjacent the viewing end 36. The flash source 102 is configured to not exceed a size to the tube 40 so as to enable insertion of the tube 40 in an inspection port 60. In an embodiment, the flash source 102 is located underneath the first lens 42 although it is understood that the flash source 102 may be positioned in other locations relative to the first lens 42 such as above or on a side of the first lens 42. Further, the flash source may emit a light pulse that is oriented along the longitudinal axis 25 or substantially transverse to the longitudinal axis 25.

Figure 11:
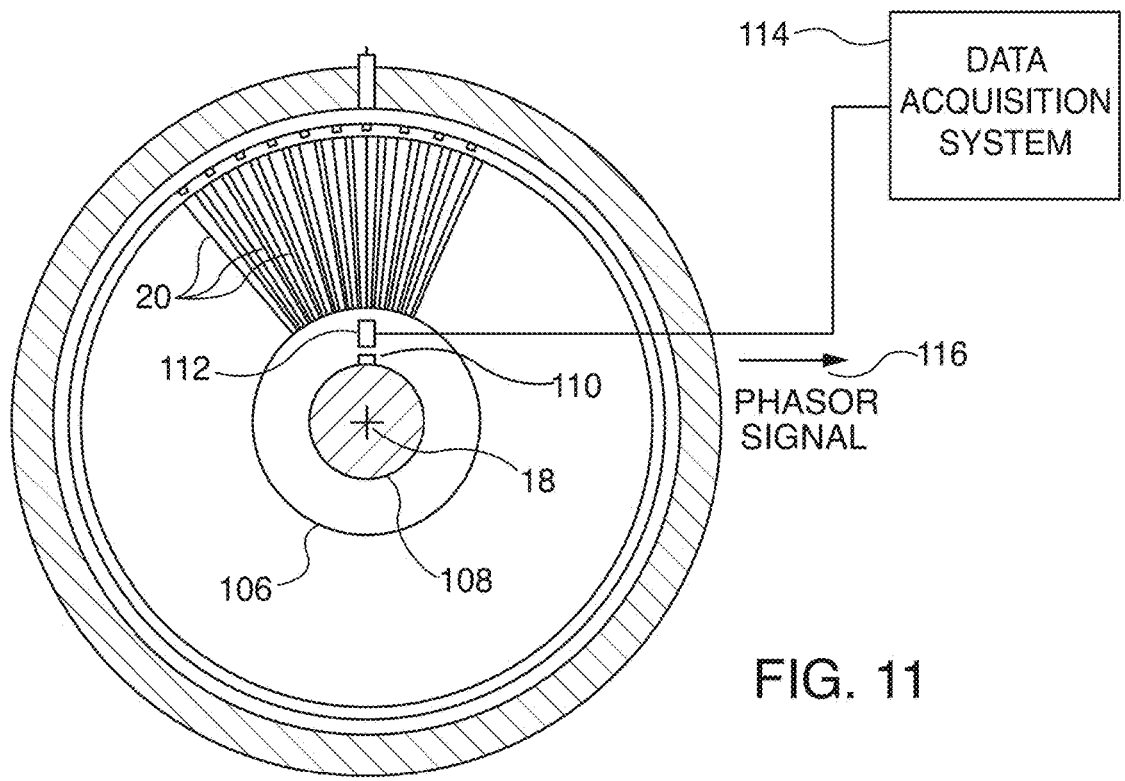
FIG. 11 is a partial cross sectional view of the turbine.

It is desirable to obtain IR images of the blades while the blades are rotating. For example, during a shutdown phase of the turbine 10, a turbine rotor rotational speed is decreased from an operating speed to a turning gear speed as part of a "turning gear mode." In this mode, the rotor is externally driven by an auxiliary drive motor in order to reduce likelihood of rotor warping. Referring to FIG. 11, a partial cross sectional view of the turbine 10 is shown. The blades 20 are attached to a rotor disk 106 which in turn is mounted to a shaft or rotor 108. The rotor 108 includes a rotor indicia 110 such as a projection or notch that operates in conjunction with a reference sensor 112 that is able to detect the presence of the rotor indicia 110 during rotation of the rotor 108 about center axis 18. This causes the generation of a phasor signal 116 that is generated once for each rotation of the rotor 108. In this regard, the disclosures of U.S. Pat. No. 7,654,145, issued Feb. 2, 2010, entitled NON-SYNCHRONOUS VIBRATIONAL EXCITATION OF TURBINE BLADES USING A ROTATING EXCITATION STRUCTURE to Michael Twerdochlib and assigned to SIEMENS ENERGY, INC., U.S. Pat. No. 7,861,592, issued Jan. 4, 2011, entitled BLADE SHROUD VIBRATION MONITOR to Michael Twerdochlib and assigned to SIEMENS ENERGY, INC. and U.S. Pat. No. 6,992,315, issued Jan. 31, 2006, entitled IN SITU COMBUSTION TURBINE ENGINE AIRFOIL INSPECTION to Michael Twerdochlib and assigned to SIEMENS ENERGY, INC. are each incorporated by reference in their entirety.

Referring to FIGS. 9 and 11, the phasor signal 116 is provided to a data acquisition system (DAS) 114 that is in communication with the computer 84. In accordance with an aspect of the invention, the flash source 102 is triggered at the appropriate time, depending on rotational speed, in order to obtain an IR image of a selected blade 20 or all the blades 20 as the blades 20 continuously rotate during one rotation of the rotor 108. In particular, the number of blades 20 in a selected row of turbine blades is input into the DAS 114. In addition, the flash source 102 is synchronized with the phasor signal 116. The flash source 102 is then triggered to provide a light pulse for each blade 20 in the selected row and at the appropriate time depending on rotational speed so as to heat each blade 20. For example, if there are 72 blades in row 1 of the turbine, the flash source is triggered 72 times at the appropriate time in order to heat each blade 20 and obtain an IR image of each blade 20 as the blades 20 rotate during one rotation of the rotor 108. If a blade 20 is not positioned in a desired location in the corresponding IR image (for example, the blade 20 is off-center in the IR image), the timing of flash source triggering may be delayed or advanced in order to obtain the desired blade location in the IR image. Alternatively, an IR image of each blade 20 or a selected blade 20 may be obtained by individually rotating the blades 20 (i.e. without continuous rotation).

Figure 12:
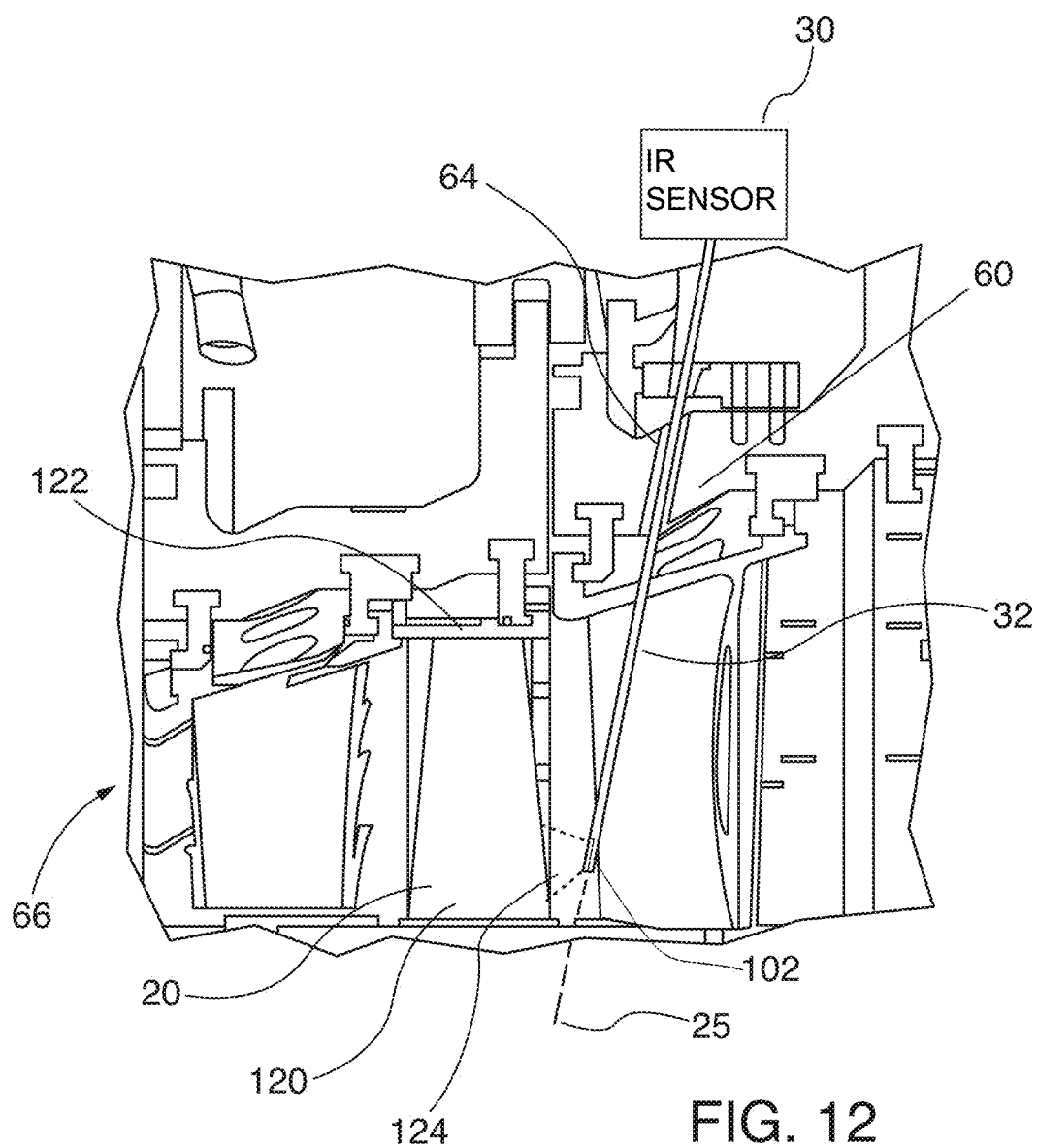
FIG. 12 is a view of the alternate embodiment in an exemplary inspection port.

Referring to FIG. 12, a partial cross sectional view of an exemplary inspection port 60 and blade 20 is shown. The port 60 includes the through hole 64 which provides access to the interior 66 of the turbine 10. In accordance with embodiments of the invention, the borescope 32, including flash source 102, is inserted into the hole 64 of the inspection port 60 to a desired depth in the turbine 10. As previously described, the flash source 102 is then triggered for each blade 20 in the selected row and at the appropriate time depending on rotational speed as previously described in order to obtain an IR image of each blade 20. Further, the borescope 32 may be moved within the inspection port 60 either radially inward toward a center of the turbine 10 or outwardly away from the center to enable the capturing of IR images between a blade platform 120 and a blade tip 122. The tube 40 provides a narrow field of view that is sufficiently localized and suitable for generating IR images suitable of cracks or other defects in a blade 20. In an embodiment, the flash source emits a light pulse 124 that is oriented substantially transverse to the longitudinal axis 25.

Thus, IR images may be captured without removal of an outer casing 62 or other disassembly of the turbine 10 to gain access to the blade 20. Further, the IR images may be obtained in situ, i.e. without having to remove the blade 20 to be imaged from the turbine 10, which results in substantial time savings.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A flash thermography device for generating an infrared image of a turbine component located inside a turbine, wherein the turbine includes at least one inspection port, comprising:
   an infrared sensor for detecting thermal energy radiated by the component;
   a borescope having sensor and viewing ends located on a longitudinal axis of the borescope, wherein the sensor end is adjacent the infrared sensor and wherein the borescope is positioned in the inspection port to locate the viewing end inside the turbine such that the component is within a field of view of the viewing end; and
   a flash source that generates a light pulse that heats the component, wherein the light pulse is oriented substantially transverse to the longitudinal axis and wherein thermal energy radiated from the component is transmitted through the borescope to the infrared sensor to enable generation of the infrared image.

2. The device according to claim 1, wherein the flash source is located adjacent the viewing end.

3. The device according to claim 2, wherein the flash source is located underneath the viewing end.

4. The device according to claim 1, wherein the borescope includes at least one lens.

5. The device according to claim 4, wherein the borescope includes at least one relay lens.

6. The device according to claim 1, wherein the infrared sensor is an infrared camera.

7. The device according to claim 1, wherein the component is a turbine blade.

8. The device according to claim 1, wherein a duration of the light pulse is approximately 2 to 15 milliseconds.

9. A flash thermography device for generating an infrared image of each of a plurality of turbine components attached to a rotor, wherein rotation of the rotor causes rotation of the components and the turbine includes at least one inspection port, comprising:
   an infrared sensor for detecting thermal energy radiated by each component;
   a borescope having at least one lens positioned between sensor and viewing ends, wherein the at least one lens and the sensor and viewing ends are located on a longitudinal axis of the borescope and wherein the sensor end is adjacent the infrared sensor and the borescope is positioned in the inspection port to locate the viewing end inside the turbine such that at least one component is within a field of view of the viewing end; and
   a flash source that generates a plurality of light pulses corresponding to the number of components that rotate during a single rotation of the rotor, wherein the light pulses are oriented substantially transverse to the longitudinal axis and each light pulse heats a corresponding component wherein thermal energy radiated from each component is transmitted through the borescope to the infrared sensor to enable generation of an infrared image of each component.

10. The device according to claim 9, wherein the single rotation of the rotor is indicated by a phasor signal.

11. The device according to claim 10 further including a data acquisition system used to synchronize the phasor signal with the generation of light pulses.

12. The device according to claim 9, wherein the components include a row of turbine blades.

13. The device according to claim 9, wherein the flash source is located adjacent the viewing end.

14. The device according to claim 13, wherein the flash source is located underneath the viewing end.

15. The device according to claim 9, wherein the borescope includes at least one relay lens.

16. The device according to claim 9, wherein a duration of the light pulse is approximately 2 to 15 milliseconds.

17. A method for generating an infrared image of each of a plurality of turbine components attached to a rotor, wherein rotation of the rotor causes rotation of the components and the turbine includes at least one inspection port, comprising:
   providing an infrared sensor for detecting thermal energy radiated by each component;
   providing a borescope having sensor and viewing ends located on a longitudinal axis of the borescope, wherein the sensor end is adjacent the infrared sensor;
   inserting the borescope in the inspection port to locate the viewing end inside the turbine such that at least one component is within a field of view of the viewing end;
   generating a phasor signal indicative of a single rotation of the rotor; and
   generating a plurality of light pulses corresponding to the number of components that rotate during a single rotation of the rotor, wherein the light pulses are oriented substantially transverse to the longitudinal axis and each light pulse heats a corresponding component wherein thermal energy radiated from each component is transmitted through the borescope to the infrared sensor to enable generation of an infrared image of each component.

18. The method according to claim 17 further including delaying or advancing generation of at least one light pulse to obtain a desired blade location in the infrared image.

19. The method according to claim 17 further including synchronizing the phasor signal with the generation of light pulses.

20. The method according to claim 17, wherein the light pulses are generated by a flash source located adjacent the viewing end.

21. A method for generating an infrared image of a turbine component located inside a turbine, wherein the turbine includes at least one inspection port, comprising:
   an infrared sensor for detecting thermal energy radiated by the component;
   a borescope having sensor and viewing ends located on a longitudinal axis of the borescope, wherein the sensor end is adjacent the infrared sensor and wherein the borescope is positioned in the inspection port to locate the viewing end inside the turbine such that the component is within a field of view of the viewing end; and
   a flash source that generates a relatively continuous flash that heats the component, wherein the flash is oriented substantially transverse to the longitudinal axis and wherein thermal energy radiated from the component is transmitted through the borescope to the infrared sensor to enable generation of the infrared image.

22. The method according to claim 21, wherein the component includes a thermal barrier coating.

23. The method according to claim 21, wherein a duration of the relatively continuous flash is approximately 1-2 minutes.

24. The method according to claim 21, wherein an increase in temperature in the component of approximately 20 degrees C generates a sufficient amount of heat suitable for obtaining an infrared image.

* * * * *